United States Patent
Matsuo et al.

(10) Patent No.: US 9,757,312 B2
(45) Date of Patent: Sep. 12, 2017

(54) METHOD OF SKIN MASSAGING

(71) Applicants: Akira Matsuo, Yokohama (JP);
Tomomi Furukawara, Yokohama (JP)

(72) Inventors: Akira Matsuo, Yokohama (JP);
Tomomi Furukawara, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 206 days.

(21) Appl. No.: 13/941,467

(22) Filed: Jul. 13, 2013

(65) Prior Publication Data
US 2013/0302388 A1 Nov. 14, 2013

Related U.S. Application Data

(63) Continuation of application No. 13/816,557, filed as application No. PCT/JP2011/066097 on Jul. 14, 2011, now abandoned.

(30) Foreign Application Priority Data

Sep. 17, 2010 (JP) ................................ 2010-209297

(51) Int. Cl.
*A61K 8/18* (2006.01)
*A61K 8/04* (2006.01)
*A61K 8/73* (2006.01)
*A61K 8/895* (2006.01)
*A61Q 19/00* (2006.01)
*A61K 8/02* (2006.01)

(52) U.S. Cl.
CPC ............ *A61K 8/042* (2013.01); *A61K 8/0241* (2013.01); *A61K 8/18* (2013.01); *A61K 8/73* (2013.01); *A61K 8/895* (2013.01); *A61Q 19/00* (2013.01); *A61K 2800/262* (2013.01)

(58) Field of Classification Search
None
See application file for complete search history.

(56) References Cited

U.S. PATENT DOCUMENTS

| | | | | |
|---|---|---|---|---|
| 5,942,215 A | * | 8/1999 | Edwards | A61K 8/0229 424/400 |
| 5,961,990 A | * | 10/1999 | Delrieu et al. | 424/401 |
| 6,319,507 B1 | * | 11/2001 | Delrieu et al. | 424/401 |
| 6,461,597 B1 | * | 10/2002 | Morita | A61K 8/025 424/401 |
| 2009/0163607 A1 | * | 6/2009 | Mine et al. | 516/98 |

FOREIGN PATENT DOCUMENTS

| | | |
|---|---|---|
| EP | 1 172 083 A2 | 1/2002 |
| EP | 1 426 027 A1 | 6/2004 |
| WO | 2007/069791 A1 | 6/2007 |

OTHER PUBLICATIONS

The International Bureau of WIPO, International Preliminary Report on Patentability, mailed in parent PCT/JP2011/066097 dated Oct. 25, 2011; English translation issued on Apr. 25, 2013.
European Patent Office, "Extended European Search Report," issued in European Patent Application No. 11 824 879.8, which is a European Counterpart of U.S. Appl. No. 13/941,467, dated May 15, 2015, 8 pages.

* cited by examiner

*Primary Examiner* — Johann R Richter
*Assistant Examiner* — Danielle Sullivan

(57) ABSTRACT

The present invention is a skin cosmetic comprising agar hydrogel particles having an average particle size of 0.2-5 mm obtained by stirring and cooling, in an oil based solvent, an agar aqueous solution prepared such that the breaking stress after the cooling/solidification is 0.005-0.1 MPa and an oil based gel prepared by mixing fine particles of silicone that are three-dimensionally cross-linked chemically and silicone oil and/or hydrocarbon oil.

The object of the present invention is to provide a cosmetic that gives a moderate massaging sensation at the time of use.

4 Claims, No Drawings

METHOD OF SKIN MASSAGING

CROSS-REFERENCE TO RELATED APPLICATIONS

This patent application is a continuation of co-pending U.S. application Ser. No. 13/816,557 filed on Feb. 12, 2013, which is a U.S. national stage entry under 35 U.S.C. §371 of International Patent Application No. PCT/JP2011/066097 filed on Jul. 14, 2011, which claims the benefit of foreign priority to Japanese Patent Application No. JP 2010-209297 filed on Sep. 17, 2010, the disclosures of all of which are hereby incorporated by reference in their entireties. The U.S. application Ser. No. 13/816,557 was published on Jun. 6, 2013, as US 2013/0142853 A1. The International Application was published in Japanese on Mar. 22, 2012, as International Publication No. WO 2012/035870 A1 under PCT Article 21(2).

TECHNICAL FIELD

The present invention relates to a skin cosmetic comprising agar hydrogel particles. More specifically, it relates to a skin cosmetic prepared by mixing agar hydrogel particles and an oil based gel to have the agar hydrogel particles dispersed in the oil based gel wherein said skin cosmetic manifests superior texture.

BACKGROUND ART

Patent Document 1 discloses a composite composition prepared by dispersing small spheres of a water based composition containing agar in a gelated or solidified oil based composition containing 12-hydroxystearic acid; it mentions that said composite composition can be used for makeup cosmetics such as lip gloss.

However, in said composite composition the oil based gel, which forms the outer phase (continuous phase), is solidified and therefore there is a concern in that, for example, the pressure of finger scooping in repeated use may gradually destroy the gel and the small spheres may precipitate. Also, since a high-viscosity oil component such as polybutene is blended into the oil based gel, which forms the outer phase (continuous phase), the spreading is heavy and stickiness tends to arise, which gives it an unfavorable texture during use as a skin care cosmetic.

Patent Document 2 discloses a skin cosmetic prepared by dispersing particles having an average particle size of 0.1-5 mm and containing agar into a transparent or semi-transparent base agent having a viscosity of 300-5,000 mPa·s.

However, it is difficult to blend a large quantity of oil components into said skin cosmetic and therefore it is very difficult to give it a skin protection effect (emollient effect) and massage effect.

On the other hand, Patent Document 3 discloses a cosmetic containing capsules enclosing an oil-in-water emulsion wherein the capsule membrane is composed of calcium alginate in the amount of 0.1-1.0 wt % relative to the total amount of the capsule.

Also, Patent Document 4 discloses a capsule-enclosed cosmetic in which barium alginate capsules, in which at least a part of the alginate exists in the form of a multivalent metal salt having barium salt as an essential ingredient, exist in the outer phase composed of a pH-adjusted aqueous solution of a carboxyvinyl polymer.

Furthermore, Patent Document 5 discloses a water-containing cosmetic containing soft capsules and spheres whose base agent is agar.

However, the alginate capsules used in Patent Documents 3 and 4 are prepared by reacting water soluble alginate with water soluble calcium salt to generate water insoluble calcium alginate, and there is a shortcoming in that, when they are applied on the skin, residue from the capsules stay on the skin to cause an unpleasant sensation.

Also, the water-containing cosmetic of Patent Document 5 is limited in terms of the blend ratio of the oil component and therefore there is a shortcoming in that it is very difficult to give it a skin protection effect (emollient effect) and/or massage effect.

PRIOR ART DOCUMENTS

Patent Documents

Patent Document 1: JP 2007-22950 A
Patent Document 2: Japanese Patent No. 3756043
Patent Document 3: JP H2-117610 A
Patent Document 4: JP H11-29433 A
Patent Document 5: JP H1-193216 A

OUTLINE OF THE INVENTION

Problem that the Present Invention Aims to Solve

In view of the aforementioned background technology, the inventors conducted earnest research to obtain a skin cosmetic having preferable texture for the purpose of skin care and discovered that a skin cosmetic prepared by mixing agar hydrogel particles and an oil based gel to have the agar hydrogel particles dispersed in the oil based gel can suppress the sensation of residue of the capsules crushed on the skin and give a good massaging sensation, that the oil based gel of the outer phase in which the agar hydrogel particles are dispersed can be thickened and gelated using a mixture of silicone cross-polymer and low viscosity silicone oil and/or hydrocarbon oil to eliminate the concern of the gel in the outer phase being destroyed and the agar hydrogel particles precipitating, and that not blending in high viscosity oil components in the oil based gel result in good spreadability and a non-sticky texture, thus completing the present invention.

The object of the present invention is to provide a cosmetic containing agar hydrogel particles that is a skin cosmetic aimed for skin care that has superior texture and gives a moderately good massaging sensation.

Means to Solve the Problem

That is, the present invention provides a skin cosmetic comprising agar hydrogel particles having an average particle size of 0.2-5 mm obtained by stirring and cooling an agar aqueous solution, prepared such that the breaking stress after the cooling/solidification is 0.005-0.1 MPa, in an oil based solvent and an oil based gel prepared by mixing fine particles of silicone that are three-dimensionally cross-linked chemically and silicone oil and/or hydrocarbon oil.

Also, the present invention provides the aforementioned skin cosmetic wherein the blend ratio of said agar hydrogel particles is 1-80 wt % of the total amount of the aforementioned skin cosmetic.

Also, the present invention provides the aforementioned skin cosmetic wherein said skin cosmetic is a massage cosmetic.

Effects of the Invention

When preparing the skin cosmetic of the present invention, an appropriate amount of the agar is blended in to have an agar aqueous solution having a specific breaking stress, which results in no remaining residue after it is applied on the skin and the agar hydrogel particles are crushed, giving a good texture and also a good and moderate massaging sensation because the agar hydrogel particles are crushed on the skin at the time of use.

Also, the oil based gel, which is to be the outer phase, is thickened and gelated by a mixture of a silicone cross-polymer and a low viscosity silicone oil and/or hydrocarbon oil; therefore the gel in the outer phase is not destroyed even with repeated use and there is no concern of the agar hydrogel particles precipitating.

Furthermore, by using a low viscosity silicone oil and/or hydrocarbon oil in the oil based gel without using a high viscosity oil component in the oil based gel, good spreadability and a non sticky texture are achieved.

THE EMBODIMENTS OF THE PRESENT INVENTION

The present invention is described in detail below.
"Agar Hydrogel Particles"

The agar hydrogel particles used in the present invention are agar hydrogel particles having an average particle size of 0.2-5 mm obtained by stirring and cooling an agar aqueous solution, prepared such that the breaking stress after the cooling/solidification is 0.005-0.1 MPa, in an oil based solvent.

The obtained agar hydrogel particles are small spheres of the hydrogel composition composed of the agar aqueous solution; since they are dispersed in the oil based solvent, they are separated by means of filtration and collected and mixed with the oil based gel, which is to be the outer phase, at room temperature to homogeneously disperse the agar hydrogel particles in the oil based gel to obtain the skin cosmetic of the present invention.

The agar aqueous solution is a water phase composition, and the agar functions as a solidifier. By using agar as the solidifier and turning the water based composition of the agar aqueous solution into hydrogel particles by the agar, the hardness of the formed agar hydrogel particles becomes suitable; when they are rubbed against the skin there is an advantage in that the residue of the agar hydrogel particles don't tend to remain and dewy freshness is given to the skin.

The blend ratio of the agar in the agar aqueous solution is preferably 0.5-5 wt %, more preferably 1.0-3.0 wt % relative to the total amount of the agar aqueous solution.

If this blend ratio is less than 0.5 wt %, then the agar aqueous solution is soft and not suitable to be solidified into agar hydrogel particles; if it is more than 5.0 wt %, then the agar hydrogel particles become too hard and collapsibility on the skin becomes poor, leading to a tendency to resist crushing and a sensation of residue arising after crushing.

In addition to water and agar, other solvent ingredients that are compatible with water, specifically lower alcohols such as ethanol, menthol, camphor and derivatives thereof (used when a fresh sensation is desired), and polyhydric alcohols such as propylene glycol, butylene glycol, and glycerin (used when moisture retention is desired) can be blended in the agar aqueous solution.

Also, as necessary, other ingredients that are compatible with water can be blended in, such as surfactants, ultraviolet protection agents, preservatives, antioxidants, pH adjustment agents, chelating agents, polymer compounds, thickeners, perfumes, and water soluble drugs.

By blending the aforementioned ingredients into the agar aqueous solution according to the purpose of the skin cosmetic, the agar hydrogel particles containing these ingredients are obtained and a skin cosmetic having a fresh sensation and moisture retaining properties can be prepared.

The aforementioned optional ingredients are blended into the agar aqueous solution in the amounts that are appropriate for the purpose. The blend ratio of water in the agar aqueous solution is not limited in particular; preferable is 1-50 wt % relative to the total amount of the agar aqueous solution.

Also, it is preferable to color the agar aqueous solution so the obtained agar hydrogel particles are colored for the purpose of making it easy to see the agar hydrogel particles dispersed in the oil based gel in the outer phase.

Coloring can be done by dispersing a pigment such as iron oxide and/or a pearl agent or by adding an oil based component to the agar aqueous solution to emulsify it, thereby turning the obtained agar hydrogel particles opaque.

The agar aqueous solution that gives a breaking stress of 0.005-0.1 MPa after cooling and solidification can be prepared by appropriately selecting the blend ratios of the agar and other water soluble optional ingredients to be blended into the agar aqueous solution, dissolving the agar and other water soluble optional ingredients in hot water, followed by cooling and solidification and checking to see if the breaking stress is in the range of 0.005-0.1 MPa.

The breaking stress is measured by using a rheometer (COMPAC-100 II from Sun Scientific Co., Ltd.) after the agar aqueous solution is cooled and solidified.

If the breaking stress is less than 0.005 MPa, then it is difficult to obtain a sufficient massaging effect; if the breaking stress is over 0.1 MPa, then the agar hydrogel particles become too hard and the collapsibility on the skin becomes poor, resulting in harder crushing and a tendency for residue to remain.

The average particle size of the agar hydrogel particles used in the present invention is 0.2-5 mm. The average particle size is a value obtained by observing the agar hydrogel particles visually or with a microscope and such and averaging the particle size of any 100 agar hydrogel particles.

To obtain the agar hydrogel particles having an average particle size of 0.2-5 mm, an agar aqueous solution dissolved in a pot at a temperature of 65-80° C. is discharged through a nozzle having an aperture of 0.5-8 mm into an oil based solvent at a temperature of approximately 40° C. in another pot. This mixture is sufficiently stirred and cooled down to approximately 30° C.; the mixture is filtered and separated and collected to obtain agar hydrogel particles having a desired average particle size.

For the oil based solvent into which the agar aqueous solution is discharged, it is preferable to use an oil component that is relatively low in viscosity and compatible with the outer phase gel, such as cyclomethicone (decamethylpentacyclosiloxane), dimethylpolysiloxane, methyiphenylpolysiloxane, and liquid paraffin.

"Oil Based Gel"

For the oil based gel used as the outer phase gel in the skin cosmetic of the present invention, a mixture of fine particles of silicone that are three-dimensionally cross-linked chemically and low viscosity silicone oil and/or hydrocarbon oil is used. It is sufficient if at least either the low viscosity silicone oil or the hydrocarbon oil is mixed with the fine particles of silicone that are three-dimensionally cross-linked chemically.

Examples of such oil based gel include the KSG series from Shin-Etsu Chemical Co., Ltd. (KSG-15, KSG-1610, KSG-16, KSG-41, KSG-42, KSG-44, KSG-210, KSG-240, KSG-310, KSG-320, KSG-330, KSG-340, KSG-710, KSG-810, KSG-820, KSG-830, and KSG-840), the silicone elastomer blend from Dow Corning Toray (9040, 9045, 9140DM, 9041, 9546, and FB-9586), and the silicone organic elastomer blend from Dow Corning Toray (EL-8040 ID and EL-8541 IN).

The blend ratio between the fine particles of silicone that are three-dimensionally cross-linked chemically and the low viscosity silicone oil and/or hydrocarbon oil in the oil based gel is not limited in particular as long as gel is formed; a preferable mass ratio is (fine particles of silicone that are three-dimensionally cross-linked chemically):(low viscosity silicone oil and/or hydrocarbon oil)=1:50 to 3:10.

For the fine particles of silicone that are three-dimensionally cross-linked chemically, specifically it is preferable to use fine particles of dimethylpolysiloxane, vinyl dimethylpolysiloxane, polyether-modified silicone, alkyl-modified silicone, and polyglycerin-modified silicone and such that are cross-linked three-dimensionally.

For the low viscosity silicone oil or hydrocarbon oil, it is preferable to use dimethylpolysiloxane, decamethylcyclopentasiloxane, isododecane, squalane, etc. having a viscosity of approximately 2-100 mPa-s at 20° C.

If the oil component of the oil based gel of the outer phase is the fine particles of silicone that are three-dimensionally cross-linked chemically and low viscosity silicone oil and/or hydrocarbon oil, or other low viscosity oil components other than these are also used but the viscosity of the oil based gel is still approximately 5,000-50,000 mPa-s at 20° C., the shortcoming of Patent Document 1 of using a high viscosity oil component is resolved and good spreadability and a non sticky texture can be manifested.

Also, oil components that can usually be used in external compositions such as cosmetics can be selected as appropriate and blended into the aforementioned oil based gel. Examples include ester oils such as cetyl-2-ethylhexanoate, 2-ethylhexyl palmitate, 2-octyldodecyl myristate, neopentyl glycol-2-ethylhexanoate, glyceryl trioctanoate, pentaerythritol tetraoctanoate, glyceryl triisostearate, glyceryl diisostearate, isopropyl myristate, myristyl myristate, and glyceryl trioleate; fats and oils such as olive oil, avocado oil, jojoba oil, sunflower oil, safflower oil, tsubaki oil, shea oil, macadamia nut oil, mink oil, lanolin, liquid lanolin, lanolin acetate, and castor oil; silicone type oil components such as cyclomethicone, dimethylpolysiloxane, methylphenylpolysiloxane, highly polymerized gum-like dimethylpolysiloxane, polyether-modified silicone, amino-modified silicone, and highly polymerized gum-like amino-modified silicone; and fluorocarbon oil components such as perfluoropolyether and perfluorocarbon.

Also, as necessary, other ingredients that are compatible with oil components can be blended into the oil based gel, such as surfactants, ultraviolet protection agents, preservatives, antioxidants, chelating agents, film forming agents, polymer compounds, perfumes, and oil based drugs.

Also, the oil based gel is preferably semi-transparent to transparent. This is because then consumers can visually confirm the agar hydrogel particles dispersed in the oil based gel and the skin cosmetic can manifest an appealing external appearance.

"Semi-transparent to transparent" in the present invention is determined by visual observation. "Semi-transparent" means the level at which the agar hydrogel particles dispersed in the oil based gel are vaguely visible and "transparent" means they can be seen clearly.

As necessary, color ingredients such as coloring agents, dyes, pearl agents, and lamella agents can be blended in within the range that the agar hydrogel particles can be visually recognized.

"Skin Cosmetic"

The skin cosmetic of the present invention is a composite composition that is the aforementioned agar hydrogel particles homogeneously dispersed in the oil based gel.

The blend ratio of the agar hydrogel particles is preferably 5-80 wt % relative to the total amount of the skin cosmetic.

The blend ratio of the oil based gel is preferably 10-80 wt % relative to the total amount of the skin cosmetic.

Furthermore, in the skin cosmetic of the present invention, the mass ratio between the agar hydrogel particles and the oil based gel is determined as appropriate for the purpose of the skin cosmetic and not limited in particular; a preferable range is (oil based gel):(agar hydrogel particles)=30:70 to 80:20.

The preparation method of the skin cosmetic of the present invention is not limited in particular; it suffices to mix the agar hydrogel particles and the oil based gel and disperse the agar hydrogel particles homogeneously in the oil based gel, which is to be the outer phase.

For example, a hose is connected to a pot that contains an agar aqueous solution, a nozzle having an aperture of approximately 0.5-8 mm is attached to the tip of the hose, and the agar aqueous solution, in a heated and melted state, is added through said nozzle into an oil based solvent, followed by stirring. With this stirring force, small sphere-like agar hydrogel particles are formed in the liquid oil component (the faster the speed of the stirring, the smaller the particle size of the small spheres), and the agar hydrogel particles in the liquid oil component are separated and collected. The collected agar hydrogel particles are added into the heated oil based gel and stirred to be homogeneously dispersed and then cooled to prepare the skin cosmetic of the present invention.

The skin cosmetic of the present invention is preferably used as a skin cosmetic for skin care containing skin care ingredients. Also, since it has a moderate massaging effect, it can also be used as a massaging cosmetic.

EXAMPLES

The present invention is described in detail below by referring to Examples. The present invention is not limited to these Examples. The blend ratio is expressed in wt % units relative to the total amount of the agar aqueous solution or the total amount of the skin cosmetic.

The jelly strength of the agar aqueous strength was measured with a rheometer (COMPAC-100 II from Sun Scientific Co., Ltd.).

Also, the average particle size of the agar hydrogel particles was visually measured.

Agar Hydrogel Particles (Hydrogel Particles 1)

| Composition | |
| --- | --- |
| 1. Ion-exchanged water | 78.5 |
| 2. Glycerin | 10 |
| 3. 1,3-butylene glycol | 4 |
| 4. Dipropylene glycol | 5 |
| 5. Agar | 2 |
| 6. Phenoxy ethanol | 0.5 |

<Preparation Method>

Ingredients 1-6 were heated up to 90° C. and dissolved. This solution was cooled down to 65° C. and discharged through a nozzle having an aperture of 8 mm into decamethylcyclopentasiloxane at 40° C.; the mixture was cooled down to 30° C. as it was stirred and the outer oil liquid was filtered out with a sifter or filtering cloth having an appropriate mesh size to obtain Agar hydrogel particles 1 (Hydrogel particles 1).

The breaking stress of the aforementioned agar aqueous solution is 0.025 MPa and the average particle size of the agar hydrogel particles is 1.5 mm.

Sodium Alginate Capsules (Hydrogel Particles 2)

| Composition | |
|---|---|
| 1 Ion-exchanged water | 79.5 |
| 2. Glycerin | 10 |
| 3. 1,3-butylene glycol | 4 |
| 4. Dipropylene glycol | 5 |
| 5. Sodium alginate | 1 |
| 6. Phenoxy ethanol | 0.5 |

<Preparation Method>

Ingredients 1-6 were heated up to 90° C. and dissolved. This solution was cooled down to 80° C. and dripped through a nozzle having an aperture of 0.5 mm into a 1% calcium chloride aqueous solution; the outer solution was filtered out with a sifter or filtering cloth having an appropriate mesh size to obtain sodium alginate capsules (Hydrogel particles 2).

The breaking stress of the aforementioned sodium alginate aqueous solution is 0.12 MPa and its average particle size is 1 mm.

<Preparation Method>

Examples 1-2, Comparative Example 3

After mixing the oil based gel and decamethylcyclopentasiloxane homogeneously, the hydrogel particles were mixed and stirred until they were homogeneous to obtain a skin cosmetic.

Comparative Examples 1-2

After a carboxyvinyl polymer was dissolved in water and neutralized by adding caustic potash, the hydrogel particles were mixed and stirred until they were homogeneous to obtain a skin cosmetic.

The evaluation method is as follows.

For all the evaluations of the textures, actual use tests (the skin cosmetics were applied on the face) with a panel of specialists (N=6) were conducted for determination and evaluation.

<Moisture Retaining (Emollient) Effect>

○: Five or more specialists of the panel evaluated that they felt the moisture retaining (emollient) effect.

Δ: Two to four specialists of the panel evaluated that they felt the moisture retaining (emollient) effect.

x: Zero to one specialist of the panel evaluated that they felt the moisture retaining (emollient) effect.

<Spreadability on the Skin>

○: Five or more specialists of the panel evaluated that they felt good spreadability on the skin.

ΔTwo to four specialists of the panel evaluated that they felt good spreadability on the skin.

TABLE 1

| | Example 1 | Example 2 | Comparative example 1 | Comparative example 2 | Comparative example 3 |
|---|---|---|---|---|---|
| (Dimethicone/Vinyl dimethicone) crosspolymer (Shin-Etsu Chemical Co., Ltd. KSG-15) *1 | 35 | | | | 35 |
| Dimethicone crosspolymer (Silicone elastomer blend 9041 from Dow Corning Toray) *2 | | 35 | | | |
| Decamethylcyclopentasiloxane (Viscosity 4 mPa-s, 20° C.) | 5 | 5 | | | 5 |
| Carboxyvinyl polymer | | | 0.3 | 0.3 | |
| Potassium hydroxide | | | 0.15 | 0.15 | |
| Ion-exchanged water | | | 39.55 | 39.55 | |
| Agar hydrogel particles (hydrogel particles 1) | 60 | 60 | 60 | | |
| Sodium alginate capsules (Hydrogel particles 2) | | | | 60 | 60 |
| Moisture retaining (emollient) effect | ○ | ○ | X | X | ○ |
| Spreadability on the skin | ○ | ○ | ○ | ○ | Δ |
| Residue remaining after application on the skin | ○ | ○ | ○ | X | X |
| Stability | ○ | ○ | ○ | X | ○ |

*1: A combination of 4 wt % of three-dimensionally cross-linked silicone composed of dimethylpolysiloxane and vinyl dimethylpolysiloxane and 96 wt % of decamethylcyclopentasiloxane (4 mPa-s (20° C.)) as a solvent for it to swell.
*2: A combination of dimensionally cross-linked silicone composed of dimethylpolysiloxane and hexadiene and dimethylpolysiloxane (5 mPa-s (20° C.)) as a solvent for it to swell.

x: Zero to one specialist of the panel evaluated that they felt good spreadability on the skin.
<Residue Remaining After Application on the Skin>
○: Five or more specialists of the panel evaluated that they didn't feel the remaining residue after application on the skin.
Δ: Two to four specialists of the panel evaluated that they didn't feel the remaining residue after application on the skin.
x: Zero to one specialist of the panel evaluated that they didn't feel the remaining residue after application on the skin.
<Perceived Massaging Effect when Applied on the Skin>
○: Five or more specialists of the panel evaluated that they felt a massaging effect after application on the skin.
Δ: Two to four specialists of the panel evaluated that they felt a massaging effect after application on the skin.
x: Zero to one specialist of the panel evaluated that they felt a massaging effect after application on the skin.
<Stability>
○: After storage for one month at −5° C. to 50° C., there is no change in color or characteristics before and after the storage.
x: After storage for one month at −5° C. to 50° C., there is substantial change in color or characteristics before and after the storage.

Agar Hydrogel Particles (Hydrogel Particles 3)

| Composition | |
|---|---|
| 1. Ion-exchanged water | 68.8 |
| 2. Glycerin | 10 |
| 3. 1,3-butylene glycol | 4 |
| 4. Dipropylene glycol | 5 |
| 5. Agar | 2 |
| 6. Phenoxy ethanol | 0.5 |
| 7. Ion-exchanged water | 0.8 |
| 8. 1,3-butylene glycol | 3.5 |
| 9. POE (60) hydrogenated castor oil | 0.4 |
| 10. Liquid paraffin | 5 |

<Preparation Method>

Ingredients 1-6 were heated up to 90° C. and dissolved. This solution was cooled down to 70° C., mixed with a mixed emulsion of 7-10, and discharged through a nozzle having an aperture of 8 mm into decamethylcyclopentasiloxane at 40° C.; the mixture was cooled down to 30° C. as it was stirred and the outer oil liquid was filtered out with a sifter or filtering cloth having an appropriate mesh size to obtain Agar hydrogel particles 2 (Hydrogel particles 3).

The breaking stress of the aforementioned agar aqueous solution is 0.02 MPa and the average particle size of the agar hydrogel particles is 1 mm.

TABLE 2

| | Example 3 | Comparative example 4 | Comparative example 5 | Comparative example 6 | Comparative example 7 |
|---|---|---|---|---|---|
| (Dimethicone/Vinyl dimethicone) crosspolymer (Shin-Etsu Chemical Co., Ltd. KSG-15) *1 | 45 | | | | |
| Decamethylcyclopentasiloxane | 5 | | | | |
| 12-hydroxystearic acid | | 1 | 3 | | |
| Dextrin palmitate | | | | 3 | |
| Glyceryl (behenate/eicosanedioate) | | | | | 3 |
| Heavy liquid isoparaffin | | 25 | | | |
| Polybutene | | 24 | | | |
| Liquid paraffin | | | 47 | 47 | 47 |
| Agar hydrogel particles (hydrogel particles 3) | 50 | 50 | 50 | 50 | 50 |
| Spreadability on the skin | ○ | X | ○ | ○ | ○ |
| Visibility of the hydrogel particles | ○ | ○ | ○ | X | X |
| Homogeneous dispersibility of the hydrogel particles in the oil phase | ○ | ○ | X | X | X |

*1: A combination of 4 wt % of three-dimensionally cross-linked silicone composed of dimethylpolysiloxane and vinyl dimethylpolysiloxane and 96 wt % of decamethylcyclopentasiloxane (4 mPa·s (20° C.)) as a solvent for it to swell.

<Visibility of the Agar Hydrogel Particles (Hydrogel Particles)>
○: The agar hydrogel particles can be visually recognized from the external appearance when the sample was put into a glass container.
x: The agar hydrogel particles cannot be visually recognized from the external appearance when the sample was put into a glass container.
<Homogeneous Dispersibility of the Agar Hydrogel Particles (Hydrogel Particles) in the Oil Phase>
○: Hydrogel particles are homogeneously dispersed in the oil phase.
x: Hydrogel particles are precipitated and not homogeneously dispersed.

The results in the aforementioned Table 1 indicate that Example 1 and Example 2 of the present invention manifest superior effects for all the evaluation items, i.e. "Moisture retaining (emollient) effect", "Spreadability on the skin", "Residue remaining after application on the skin", and "Stability."

<Preparation Method>

Example 3

After mixing (dimethicone/vinyl dimethicone) crosspolymer and cyclomethicone homogeneously, the hydrogel particles were mixed and stirred until they were homogeneous to obtain a skin cosmetic.

Comparative Examples 4-7

12-hydroxystearic acid, dextrin palmitate, glyceryl (behenate/eicosanedioate), etc. were added to a liquid oil component that had been heated up to 90° C., and melted; after cooling down to approximately 70 degrees, the hydrogel particles were mixed and left at rest to solidify to obtain a skin cosmetic.

The results in Table 2 indicate that only Example 3 that uses an oil based gel prepared by mixing fine particles of silicone chemically cross-linked three-dimensionally ((dimethicone/vinyl dimethicone) crosspolymer) and a low viscosity silicone oil (decamethylcyclopentasiloxane) is superior to Comparative example(s) using other oil components in all the evaluation items of "spreadability on the skin", "visibility of the hydrogel particles", and "homogeneous dispersibility of the hydrogel particles in the oil phase."

Agar Hydrogel Particles (Hydrogel Particles 4-7)

TABLE 3

| | Agar hydrogel particles (hydrogel particles 4-7) | 4 | 5 | 6 | 7 |
|---|---|---|---|---|---|
| 1 | Ion-exchanged water | 80.1 | 79.5 | 78.5 | 75.4 |
| 2 | Glycerin | 10 | 10 | 10 | 10 |
| 3 | 1,3-butylene glycol | 4 | 4 | 4 | 4 |
| 4 | Dipropylene glycol | 5 | 5 | 5 | 5 |
| 5 | Agar (CS-110 from Ina Food Industry, Co., Ltd.) | 0.4 | | 2 | 5.1 |
| 6 | Agar (PS-84 from Ina Food Industry, Co., Ltd.) | | 0.5 | | |
| 7 | Phenoxy ethanol | 0.5 | 0.5 | 0.5 | 0.5 |
| | Breaking stress of the agar aqueous solution (MPa) | 0.0035 | 0.015 | 0.024 | 0.14 |
| | Average particle size of the agar hydrogel particles (mm) | 1.5 | 1.5 | 1.5 | 1.5 |

<Preparation Method>

Ingredients 1-6 were heated up to 90° C. and dissolved. This solution was cooled down to 65° C. and discharged through a nozzle having an aperture of 8 mm into decamethylcyclopentasiloxane at 40° C.; the mixture was cooled down to 30° C. as it was stirred and the outer oil liquid was filtered out with a sifter or filtering cloth having an appropriate mesh size to obtain each group of Agar hydrogel particles (Hydrogel particles 4-7).

TABLE 4

| | Example 4 | Example 5 | Comparative example 8 | Comparative example 9 |
|---|---|---|---|---|
| (Dimethicone/Vinyl dimethicone) crosspolymer (Shin-Etsu Chemical Co., Ltd. KSG-15) *1 | 50 | 50 | 50 | 50 |
| Agar hydrogel particles (hydrogel particles 4) | | | 50 | |
| Agar hydrogel particles (hydrogel particles 5) | 50 | | | |
| Agar hydrogel particles (hydrogel particles 6) | | 50 | | |
| Agar hydrogel particles (hydrogel particles 7) | | | | 50 |
| Perceived massaging effect when applied on the skin | ◯ | ◯ | X | ◯ |
| Residue remaining after application on the skin | ◯ | ◯ | ◯ | X |

*1: A combination of 4 wt % of three-dimensionally cross-linked silicone composed of dimethylpolysiloxane and vinyl dimethylpolysiloxane and 96 wt % of decamethylcyclopentasiloxane (4 mPa-s (20° C.)) as a solvent for it to swell.

<Preparation Method>

The (dimethicone/vinyl dimethicone) crosspolymer and the agar hydrogel particles were mixed at room temperature to obtain skin cosmetics of Examples and Comparative examples.

Comparative example 8 and Comparative example 9, in which the breaking stress of the agar aqueous solution is not within the range defined by the present invention (0.005-0.1 MPa), are inferior in terms of the effects of "perceived massaging effect after application on the skin" and "residue remaining after application on the skin."

In contrast, Example 4 and Example 5, in which the breaking stress of the agar aqueous solution meets the requirement of the present invention, are indicated to have superior effects in terms of "perceived massaging effect after application on the skin" and "residue remaining after application on the skin."

INDUSTRIAL APPLICATIONS

The skin cosmetic of the present invention has a superior texture due to specific agar hydrogel particles dispersed in a specific oil based gel; and it is very useful as a skin cosmetic having excellent visibility of the agar hydrogel particles. In particular, it has a high utility value as a massaging cosmetic for skin care giving a moderate massaging sensation.

The invention claimed is:

1. A method of skin massaging, comprising the step of:
   crushing agar hydrogel particles on the skin by applying a massaging cosmetic containing the agar hydrogel particles and an oil based gel;
   wherein:
   the agar hydrogel particles have an average particle size of 0.2-5 mm obtained by stirring and cooling, in an oil based solvent, an agar aqueous solution prepared such that the breaking stress after the cooling/solidification is 0.015-0.024 MPa;
   the oil based gel is prepared by mixing:
     fine particles of three-dimensionally cross-linked silicone composed of dimethylpolysiloxane and vinyl dimethylpolysiloxane; and
     decamethylcyclopentasiloxane as silicone oil, and/or hydrocarbon oil;
   the mass ratio between the fine particles of three-dimensionally cross-linked silicone and the silicone oil and/or hydrocarbon oil in the oil based gel is (fine particles of three-dimensionally cross-linked silicone):(silicone oil and/or hydrocarbon oil)=1:50 to 3:10;
   the oil based gel has a viscosity of approximately 5,000-50,000 mPa s at 20° C.;
   the blend ratio of the agar hydrogel particles is 5-80 wt % relative to the total amount of the massaging cosmetic;
   the blend ratio of the oil based gel is 10-80 wt % relative to the total amount of the massaging cosmetic;
   the mass ratio between the agar hydrogel particles and the oil based gel is (oil based gel):(agar hydrogel particles)=30:70 to 80:20;
   the oil based gel is semi-transparent to transparent; and
   the agar hydrogel particles are dispersed in the oil based gel and are visually observable.

2. The method according to claim 1, wherein the massaging cosmetic further contains a color ingredient.

3. A method of skin massaging, comprising the step of:
   crushing agar hydrogel particles on the skin by applying a massaging cosmetic containing the agar hydrogel particles and an oil based gel;
   wherein:
   the agar hydrogel particles have an average particle size of 0.2-5 mm obtained by stirring and cooling, in an oil based solvent, an agar aqueous solution prepared such that the breaking stress after the cooling/solidification is 0.015-0.024 MPa;

the oil based gel is prepared by mixing:
 fine particles of three-dimensionally cross-linked silicone composed of dimethylpolysiloxane and hexadiene; and
 dimethylpolysiloxane as silicone oil, and/or hydrocarbon oil;
the mass ratio between the fine particles of three-dimensionally cross-linked silicone and the silicone oil and/or hydrocarbon oil in the oil based gel is (fine particles of three-dimensionally cross-linked silicone):(silicone oil and/or hydrocarbon oil)=1:50 to 3:10;
the oil based gel has a viscosity of approximately 5,000-50,000 mPa s at 20° C.;
the blend ratio of the agar hydrogel particles is 5-80 wt % relative to the total amount of the massaging cosmetic;
the blend ratio of the oil based gel is 10-80 wt % relative to the total amount of the massaging cosmetic;
the mass ratio between the agar hydrogel particles and the oil based gel is (oil based gel):(agar hydrogel particles)=30:70 to 80:20;
the oil based gel is semi-transparent to transparent; and
the agar hydrogel particles are dispersed in the oil based gel and are visually observable.

4. The method according to claim 3, wherein the massaging cosmetic further contains a color ingredient.

* * * * *